US010393886B2

(12) United States Patent
MacLaughlin

(10) Patent No.: US 10,393,886 B2
(45) Date of Patent: Aug. 27, 2019

(54) METHOD AND APPARATUS FOR AUTOMATIC TOUCHLESS WIRELESS CHARGING OF MOBILE X-RAY CART DETECTORS AND ACCESSORIES

(71) Applicant: CARESTREAM HEALTH, INC., Rochester, NY (US)

(72) Inventor: Scott T. MacLaughlin, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 224 days.

(21) Appl. No.: 15/497,495

(22) Filed: Apr. 26, 2017

(65) Prior Publication Data
US 2018/0059258 A1 Mar. 1, 2018

Related U.S. Application Data

(60) Provisional application No. 62/378,929, filed on Aug. 24, 2016.

(51) Int. Cl.
*G01T 1/175* (2006.01)
*H02J 7/02* (2016.01)
*H02J 7/00* (2006.01)
*G01N 23/04* (2018.01)

(52) U.S. Cl.
CPC .............. *G01T 1/175* (2013.01); *G01N 23/04* (2013.01); *H02J 7/0021* (2013.01); *H02J 7/025* (2013.01); *H02J 7/027* (2013.01); *G01N 2223/50* (2013.01); *H02J 2007/0096* (2013.01)

(58) Field of Classification Search
CPC .... G01T 1/175; G01N 23/04; G01N 2223/50; H02J 7/0021; H02J 7/027; H02J 2007/0096
USPC ....................... 328/98.8, 101–103, 193–198; 250/370.08, 370.09
See application file for complete search history.

(56) References Cited

U.S. PATENT DOCUMENTS

| 6,127,799 | A | 10/2000 | Krishnan |
| 7,383,064 | B2 | 6/2008 | Mickle et al. |
| 8,115,448 | B2 | 2/2012 | John |
| 2013/0301803 | A1* | 11/2013 | Liu .......................... A61B 6/42 378/114 |
| 2015/0214765 | A1 | 7/2015 | Perry |

* cited by examiner

Primary Examiner — Courtney D Thomas

(57) ABSTRACT

A mobile radiography system has a moveable transport frame configured to travel across a floor. An adjustable support structure is coupled to the moveable transport frame and an x-ray source is coupled to the adjustable support structure. A power transmitter emits wireless power signals to a digital detector to charge a battery therein. Power signal receiving circuitry in the detector receives the wireless power signals to generate recharging current for the battery.

20 Claims, 7 Drawing Sheets

METHOD AND APPARATUS FOR AUTOMATIC TOUCHLESS WIRELESS CHARGING OF MOBILE X-RAY CART DETECTORS AND ACCESSORIES

CROSS REFERENCE TO RELATED APPLICATIONS

This application claims the benefit of U.S. Provisional Application No. 62/378,929, filed Aug. 24, 2016, entitled METHOD AND APPARATUS FOR AUTOMATIC TOUCHLESS WIRELESS CHARGING OF MOBILE X-RAY CART DETECTORS AND ACCESSORIES in the name of Scott T. MacLaughlin, which is hereby incorporated by reference herein in its entirety.

TECHNICAL FIELD

The disclosure relates generally to the field of mobile radiographic imaging and, more particularly, to contactless recharging of wireless digital detectors.

BACKGROUND

Mobile digital radiography x-ray carts typically carry multiple wireless digital radiography (DR) detectors of different sizes. The detectors are secured in multiple uniquely sized bins or slots built into the cart. Because the detectors' rechargeable battery power is depleted during use, each detector bin typically contains a charging port that physically electrically engages a corresponding connector in the detector to recharge its battery between patient exams.

This conventional method of charging is restrictive in that it requires (1) a separate bin per detector size, which may or may not be utilized for a particular cart; (2) matching electrical connectors on the cart (power transmitters) and detector (power receiver) for each bin; (3) a single insertion orientation of the detector into the bin to align the matching connector and charging port, i.e., not backwards or upside down, since the detector(s) can only be charged when properly inserted into the bin. In addition, many digital radiography x-ray carts are retrofitted, meaning that an analog x-ray cart has been converted into a digital radiography cart. In this instance, the original cart bin does not contain any charging mechanism (since it was designed for film cassettes). For such a cart, extra rechargeable batteries need to be carried, at additional cost and space requirements, to enable the detector to retain battery power for least one examination round.

Finally, mobile digital radiography x-ray carts also utilize other devices that require battery power, such as barcode readers, manual prep/expose switches, removable tablets, grids, etc. which must be tethered or inserted into a unique charging port to be powered and/or to recharge. A potential solution is the use of traditional conductive/inductive wireless charging, however, this solution requires that the device(s) to be charged must be in direct physical contact with a charging transmitter which can typically only charge one device at a time.

Thus, there is a need for improved apparatus and methods for DR detector recharging that can overcome the limitations of current practices. The discussion above is merely provided for general background information and is not intended to be used as an aid in determining the scope of the claimed subject matter.

SUMMARY

An object of the present disclosure is to address the need for wireless DR detector recharging, particularly suitable for mobile radiography apparatuses and applications.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

In one embodiment, a mobile radiography system includes a moveable transport frame for rolling across a floor, an adjustable column coupled to the transport frame, an x-ray source coupled to the adjustable column, and a power transmitter to transmit wireless power signals. A battery powered digital detector used to capture radiographic images generated by the x-ray source is recharged by the wireless power signals.

In one embodiment, a mobile radiography system includes a moveable transport frame for rolling across a floor, an adjustable support coupled to the moveable frame, an x-ray source coupled to the adjustable support, a battery powered electronic device associated with the mobile radiography system, and a power transmitter with one or more antennas to transmit wireless power signals. A digital transponder is configured to transmit a polling signal to the electronic device and to receive a response signal indicating a battery charge level of the device's battery. The digital transponder determines a relative location of the electronic device if its response signal indicates a low battery charge level. The digital transponder can then align one or more antennas to focus the wireless power signals toward the battery powered electronic device.

In one embodiment, a method of recharging a battery powered electronic device includes wirelessly communicating with the battery powered electronic device and determining its charge level. Wireless power signals are transmitted to the battery powered electronic device if its charge level is below a preselected threshold. A charge level of the battery powered electronic device is monitored while transmitting the wireless power signals. The transmitting is terminated when the charge level rises above a preset threshold.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE EMBODIMENTS

Figure 1:
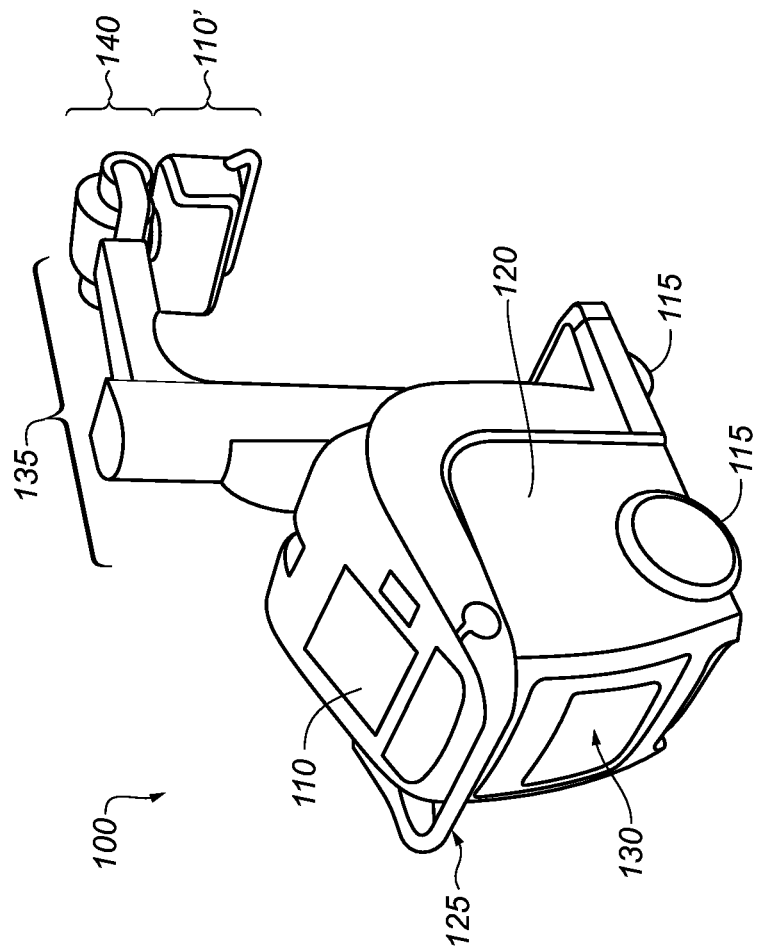
FIG. 1 is a perspective view that shows an exemplary mobile radiography unit according to one embodiment.

The following is a detailed description of the preferred embodiments, reference being made to the drawings in which the same reference numerals identify the same elements of structure in each of the several figures.

Where they are used in the present disclosure, the terms "first", "second", and so on, do not necessarily denote any ordinal, sequential, or priority relation, but are simply used to more clearly distinguish one element or set of elements from another, unless specified otherwise.

As used herein, the term "energizable" relates to a device or set of components that perform an indicated function upon receiving power and, optionally, upon receiving an enabling signal.

Reference is hereby made to
- U.S. Pat. No. 8,115,448 entitled "Systems and Methods for Wireless Power" to John;
- U.S. Pat. No. 6,127,799 entitled "Method and Apparatus for Wireless Powering and Recharging" to Krishnan;
- U.S. Pat. No. 7,383,064 entitled "Recharging Method and Associated Apparatus" to Mickle et al.;
- US Patent Application Publication No. 2015/0214765 entitled "Focus Control for Wireless Power Transfer" by Perry.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

Embodiments of the present invention utilize recent advances in touchless wireless power transmission to automatically charge digital radiography detectors and accessories simultaneously without wired electrical connections, and without unique orientation or location of the accessories in, on or near the mobile x-ray cart. An omni-directional transmitter located on the mobile x-ray cart may transmit energy via radio frequency signals in the gigahertz range to specially configured electronic devices such as digital radiography detectors, barcode readers, tablets, prep/expose switches, and grids. The electronic devices may be required to be within a specified range from the transmitter, such as a distance of 30 feet. The electronic device being charged may also be stationary or moving while being wirelessly charged. The associated wireless power receiver in each electronic device may be configured to convert the received RF signals from the transmitter into an electric current that recharges an internal battery at the same rate as if the internal battery was plugged into a wall outlet, or an electrical power source such as provided in a detector bin in a mobile radiography cart. The wireless charging system may be enabled for "on demand" charging of each wireless electronic device, meaning that the RF transmitter will only transmit a charging RF signal to a wireless electronic device after the wireless charging system receives a recharge request transmitted by the wireless electronic device. The wireless electronic device may be programmed, for example, to transmit the recharge request when the wireless electronic device detects an internal battery power drop to 50% of its battery capacity. The wireless electronic devices may use standard size batteries that are interchangeable among the several wireless electronic devices. This can be advantageous for the mobile digital radiography x-ray cart as other devices may be secured on the cart, such as a flashlight, handheld pulse oximeter, or other battery powered medical or non-medical devices. Because the disclosed apparatus and method of recharging may be enabled using a 30 foot radius between the charging transmitter and the wireless electronic device, the wireless electronic devices undergo an increased charge time duration as compared to being charged only when they are properly inserted into a corresponding recharge slot in a mobile x-ray cart. For example, a wireless digital detector's internal battery can be recharged while the detector is being used to capture radiographic images of a patient.

The digital radiography x-ray cart's power transmitter may be used to recharge specifically configured wireless devices in its vicinity, such as TV remote controls in patient rooms, cell phones, laptops, etc. at a nurse's station. For example, recharging can be undertaken in any electronic hand-held device having a rechargeable battery and power signal conversion circuitry to receive the wireless power signals and to convert the signals into a recharge current for recharging a battery thereby. Because the mobile digital radiography x-ray cart is typically moved throughout a medical facility, it can automatically and wirelessly recharge any specially configured device within the cart's chargeable range.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

FIG. 1 is a perspective view of a mobile radiography apparatus 100 that may include multiple portable radiographic detectors, or flat panel detectors, secured therein (FIG. 2) according to embodiments of the present application. The exemplary mobile x-ray or radiography apparatus 100 of FIG. 1 may be employed for computed radiography (CR) and/or digital radiography (DR).

As shown in FIG. 1, the mobile radiography apparatus 100 (cart) can include a moveable transport frame 120 that includes a first digital display 110, or digital monitor, and an optional second digital display 110' at the x-ray tube head to display relevant information such as captured radiographic images and related data such as alphanumeric information. As shown in FIG. 1, the second display 110' may be pivotably mounted at the x-ray tube head proximate the x-ray source 140 to be viewable/touchable from a 360 degree area. In one embodiment, the x-ray source 140 may include a collimator and a collimator light used to illuminate an area on a subject to be radiographically imaged.

The displays 110, 110' may implement or provide input control (e.g., touch screens) functions to initiate generating, storing, transmitting, modifying, and printing of any captured image(s) and may include an integral or separate control panel (not shown) to assist in implementing functions such as generating, storing, transmitting, modifying, and printing of an obtained radiographic image(s).

For mobility, the mobile radiographic apparatus 100 may include one or more wheels 115 and one or more handle grips 125, typically provided at waist-level, arm-level, or hand-level, that allows an operator to roll the mobile radiographic apparatus 100 over a surface such as a floor to a desired location. A self-contained battery pack (e.g., rechargeable) may provide source power, which may reduce or eliminate the need for operation near a power outlet. The on-board self-contained battery pack can provide power to electric motors configured to drive the wheels 115 for motorized transport of the mobile radiography unit 100.

As described hereinbelow, the mobile radiographic apparatus 100 may include bins or slots for holding/storing one or more digital radiographic (DR) detectors or computed radiography cassettes. The mobile radiographic apparatus 100 may include a storage area 130 (e.g., disposed on the transport frame 120) configured to removably retain one or more digital radiography (DR) detectors. The storage area 130 may be configured to hold a plurality of different sized detectors and the mobile radiographic apparatus 100 may also be configured to transmit wireless power to the multiple DR detectors in the storage slots.

Mounted to the transport frame 120 is a support structure including a vertical support column and horizontal boom 135, coupled to the frame 120 and providing a structure that supports the tube head which includes x-ray source 140 and display 110'. In the embodiment shown in FIG. 1, the column and boom 135 may include an adjustable boom configured to ride vertically up and down the column section to a desired height for obtaining images. In another embodiment, the tube head, or x-ray source 140, may be rotatably coupled to the column and boom 135 support structure. In another exemplary embodiment, an articulated member that bends at a joint mechanism can allow movement of the x-ray source 140 over a range of vertical and horizontal positions. Height settings for the x-ray source 140 can range from low height for imaging feet and lower extremities to shoulder height and above for imaging upper body portions of patients.

Figure 2:
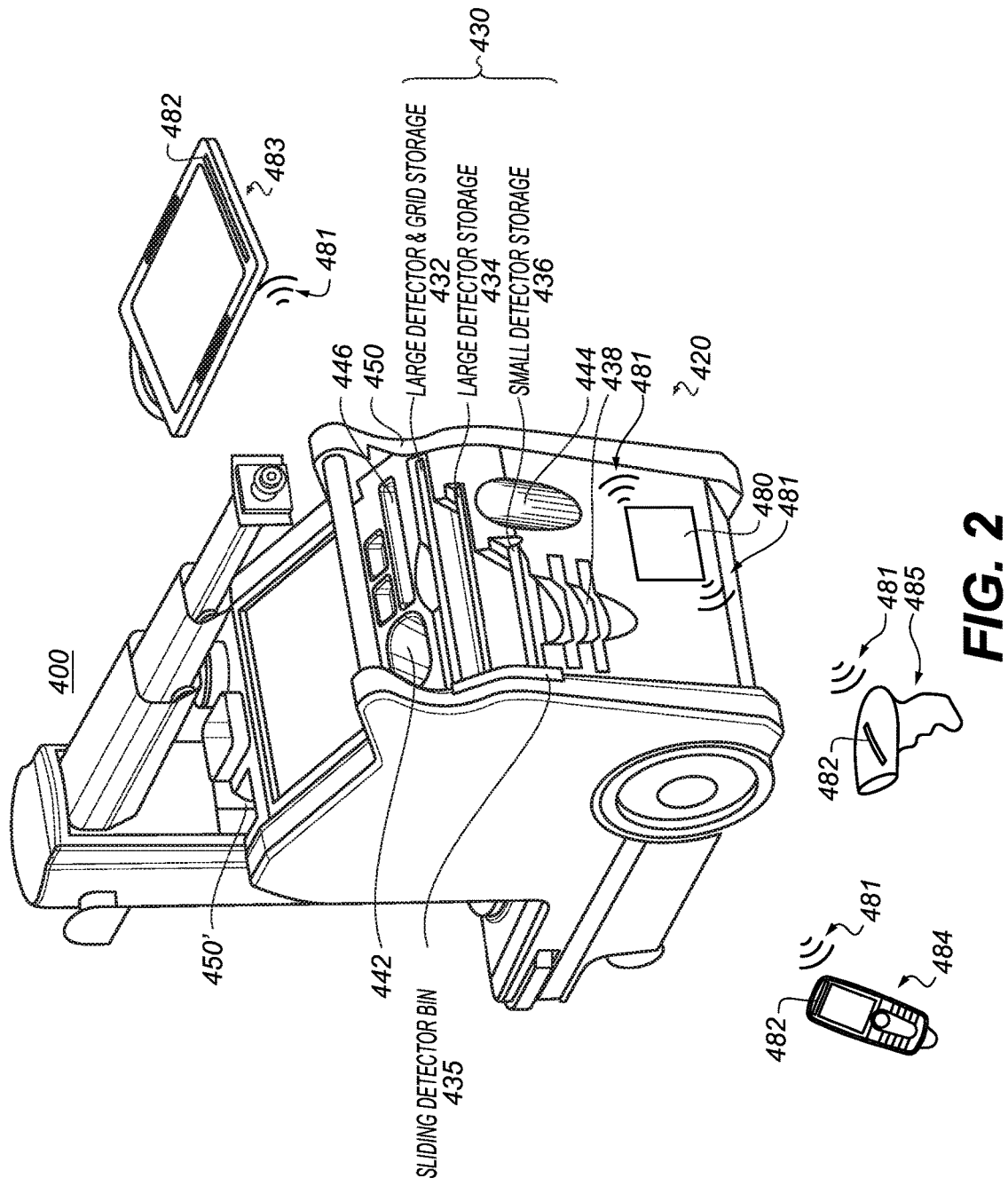
FIG. 2 is a diagram that illustrates an embodiment of an exemplary wireless power transmission system for a mobile radiographic cart system.

FIG. 2 is a diagram of a wireless power transmission apparatus and method for a mobile radiographic system 400 according to the present application. The mobile radiographic system 400 is illustrated in FIG. 2 without an x-ray source 140 or display 110' for ease of illustration. As shown in FIG. 2, a mobile radiography system 400 may include a moveable transport frame 420 that includes storage area 430 for different sized detectors that include bins 435 configured to receive detectors inserted therein. The storage area 430 can include a plurality of individual slots such as detector holder storage or large detector and grid storage 432, large detector storage 434, and/or small detector storage 436 that may receive an inserted detector. Exemplary detector bins may include a detector with/without a grid and/or additional detector accessories such as but not limited to additional antenna, power supply or additional electronics. The bins 435 can be configured in an unlocked mode where detectors can be freely removed from the storage area and a locked mode where detectors cannot be freely removed from the storage bin 435. In one embodiment, the storage area 430 can include an area for battery charge slots 438 where at least one battery removed from detectors 483 can be recharged by the mobile radiography apparatus 400. Additional storage areas at the mobile radiography apparatus 400 can include storage 442, e.g., for pulse oximeters 484, barcode scanners 485, or other devices. A bag storage area 444, and additional storage 446 may also be provided. The mobile radiography apparatus 400 can also include a wired prep/expose control switch 450 and a remote prep/expose control 450'. Rechargeable batteries may be interchangeable between digital detectors 483.

As shown in FIG. 2, the mobile radiography cart 400 may be configured with a wireless power transmission device 480 to transmit RF power signals 481 to various digital devices such as x-ray detectors 483 provided with configured electronics 482 to enable receiving and converting the transmitted RF power signals into a recharging current for batteries in the devices. The rechargeable devices may include x-ray detectors 483, pulse oximeters 484, or barcode scanners 485, for example. The electronics 482 in the digital devices may include dedicated integrated circuit chips capable of detecting an appropriate frequency of the wireless power signals 481 and to convert the signals into an appropriate charging current for rechargeable batteries in the devices 483-485. The electronics 482 may include an onboard IC chip or chipset, or the electronics 482 may be embodied in an attachment that is electrically connected to the devices 483-485, such as a wired port attachment or a sleeve wherein the devices 483-485 may be inserted. The electronics 482 may be embodied within a rechargeable battery assembly such that a replacement battery back includes the receiving electronics 482 to enable receiving the RF power signals 481 and providing a recharging current for the battery in the rechargeable battery assembly.

The wireless power transmission device 480 may include an omni-directional transmission embodiment wherein the RF power signals are transmitted in all directions using an antenna or it may include a directed power transmission assembly including an array of directed antennas configured to direct wireless power signals in predetermined directions aimed at the receiving digital devices 483-485 or aimed to converge at the receiving digital devices 483-485, such as by intentional reflection of the RF power signals 481. The array of antennas may include micro-antennas configured to transmit RF power signals over a distance of about 30 feet and up to about 1 watt of recharging power.

The receiving devices 483-485 may include wireless transceivers therein for transmitting data such as instructions, commands, and/or requests to a processing system of the mobile radiography cart 400. The receiving devices 483-485 may each further include digital battery power monitoring circuitry to detect a remaining power level of the device battery, which may be measured as a percentage of remaining battery power.

According to an embodiment of the present disclosure, a number of digital detectors are each stored in a corresponding storage bin in the moveable transport frame of mobile radiographic system 400. Each of the digital detectors is configured to capture a radiographic image generated by x-rays from the x-ray source and may be configured to have different rechargeable batteries and power signal receiving circuits to receive wireless power signals.

The receiving devices 483-485 may each be further configured to transmit a request to the mobile radiography cart 400 to begin transmission of RF power signals 481. The receiving devices 483-485 may each be further configured to monitor remaining battery power and to transmit such a request when the monitored battery power reaches a preselected threshold, such as 50% remaining battery power, or any other desired level of remaining battery power. The receiving devices 483-485 may each further include individual communication channels to separately communicate with the processing system of the mobile radiography cart 400 for individual control/request operation of the receiving devices 483-485. The receiving devices 483-485 may each be configured to receive RF power signals of a preselected frequency, such as 2.4 GHz or 5.8 GHz, for example. The receiving devices 483-485 may each be further configured to monitor a frequency of the transmitted RF power signals 481 and to selectively receive the RF power signals for recharging purposes only if the frequency of the RF power signals matches the device's preselected frequency.

As disclosed herein, the present invention discloses apparatus and method embodiments wherein a mobile x-ray cart radiographic imaging system is configured to charge all digital wireless devices in its vicinity that are adapted to receive and convert the received wireless power signals, or it may be configured to charge other medical or non-medical devices within a configured range of the x-ray cart that use standard battery sizes containing a configured power receiver.

In one embodiment, devices forming a portion of the mobile radiography system 100, 400 may also contain elements requiring electrical power to operate. One such example is the collimator light described above. For example, powering the collimator light may require that a cable be routed from the power source in the cart base, or transport frame 120, through the multiple sections of the column and telescoping arms of boom 135. Complicated cable harnesses, especially ones that have to be moved or translated, may comprise one of the highest failure modes on a mobile x-ray cart, ultrasound cart, or other x-ray system. Instead of using cabling to transfer power, the RF power signals as disclosed herein may be used to wirelessly transmit power simultaneously with control signals to avoid the need for costly and failure-prone cabling. This may also save space, cost, and assembly time for routing cables. Power signal receiving electronics 482 would need to be added to system elements such as the collimator light, or the power source of the collimator light, such as a non-standard custom battery or standard battery, such as an AA battery, for example, that contains power receiving and conversion circuitry for the RF power signals.

Alternately, a rechargeable battery can be configured to be removed from a corresponding digital detector in order to receive wireless power signals that recharge the rechargeable battery. Once recharged, the battery can then be re-installed.

The disclosed embodiments may eliminate the requirement for physical connectors and ports to charge devices, and may allow the devices to be located in spatial proximity to the mobile radiography cart. This may save cart cost, complexity, and improve reliability as well as flexibility of where devices may be located. The need to tether, via wires and cables, powered cart devices may be eliminated. As electrical connectors are prone to fluid damage and can be a major source of fluid ingress, the elimination of these electrical external ports enables improved fluid ingress protection and the ability to meet more robust IPX (Ingress Protection) ratings. The devices to be charged are also allowed to be in motion—an operator may carry a detector, grid, or a barcode reader while it is receiving wireless recharging power signals.

Figure 3:
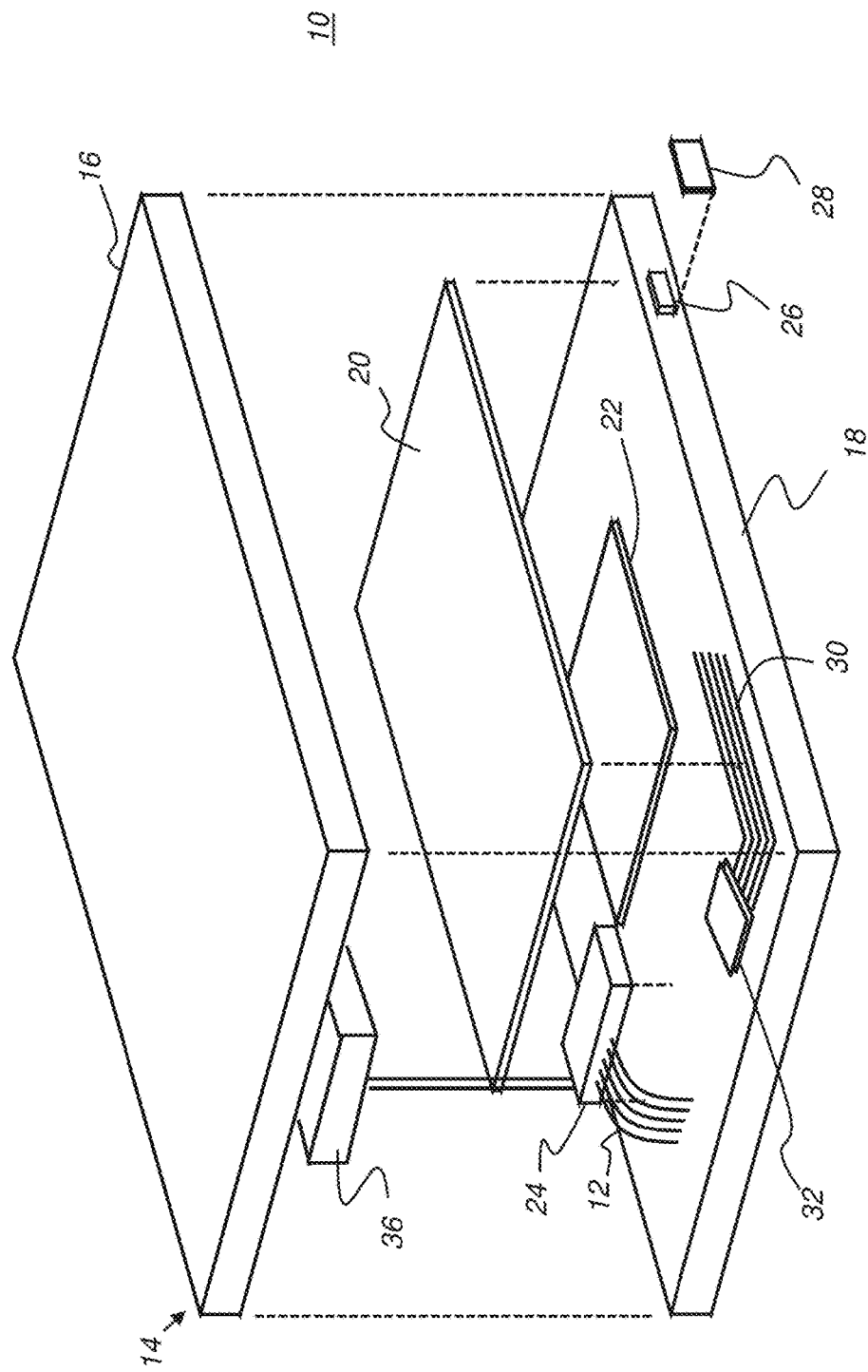
FIG. 3 is a perspective exploded view showing components of an exemplary digital radiography detector configured for wireless charging.

The exploded view of FIG. 3 shows, in simplified form, some of the electrically active internal components of a DR detector 10 that are protected within an enclosure or housing 14 formed using multiple parts, including top and bottom covers 16 and 18. A detector array 20 includes a scintillator layer that outputs visible light energy when energized by x-rays impacting the scintillator. Another layer of the detector array 20 includes a two-dimensional array of electromagnetic radiation (light) sensitive elements for capturing image data from the output light energy received from the scintillator. A circuit board 22 provides supporting control electronics for reading out and storing the image data captured by the light sensitive elements. The circuit board may further include wireless transmission capability for sending the captured image data to an external host system. A rechargeable battery 24 provides power, acting as the voltage source for detector 10 operations. A port 26 extending through bottom cover 18 is provided to allow electrical connection to a cable for receiving and transmitting data, and/or receiving power for operation and for battery charging, such as from an external voltage supply. The port 26 may have an optional cover plate or sealing cap 28, which may be a rubber seal or other liquid-proofing material. In addition to the illustrated components, a number of interconnecting cables, supporting fasteners, protective cushioning materials, connectors, and other elements may be included in a completed version of the DR detector 10. An optional antenna 30 and transmitter 32, external to and electrically connected to the circuit board 22, for wireless communication may alternately be provided, with antenna 30 extending within the housing 14. One or more cables 12, such as multi-wire flexible ribbon cables, may also be included within housing 14 for interconnection between components.

For wireless recharging, a charging coupler 36 provides power signal receiving circuitry that includes an antenna and other components. Coupler 36 can also monitor battery 24 power levels and provide recharging current to battery 24. The charging current may be obtained from energy in an electromagnetic field transmitted by a wireless current source, such as from power transmission device 480 (FIG. 2). Charging coupler 36 may be, for example, an inductive coupler that provides power at suitable levels for DR detector 10.

Figure 4:
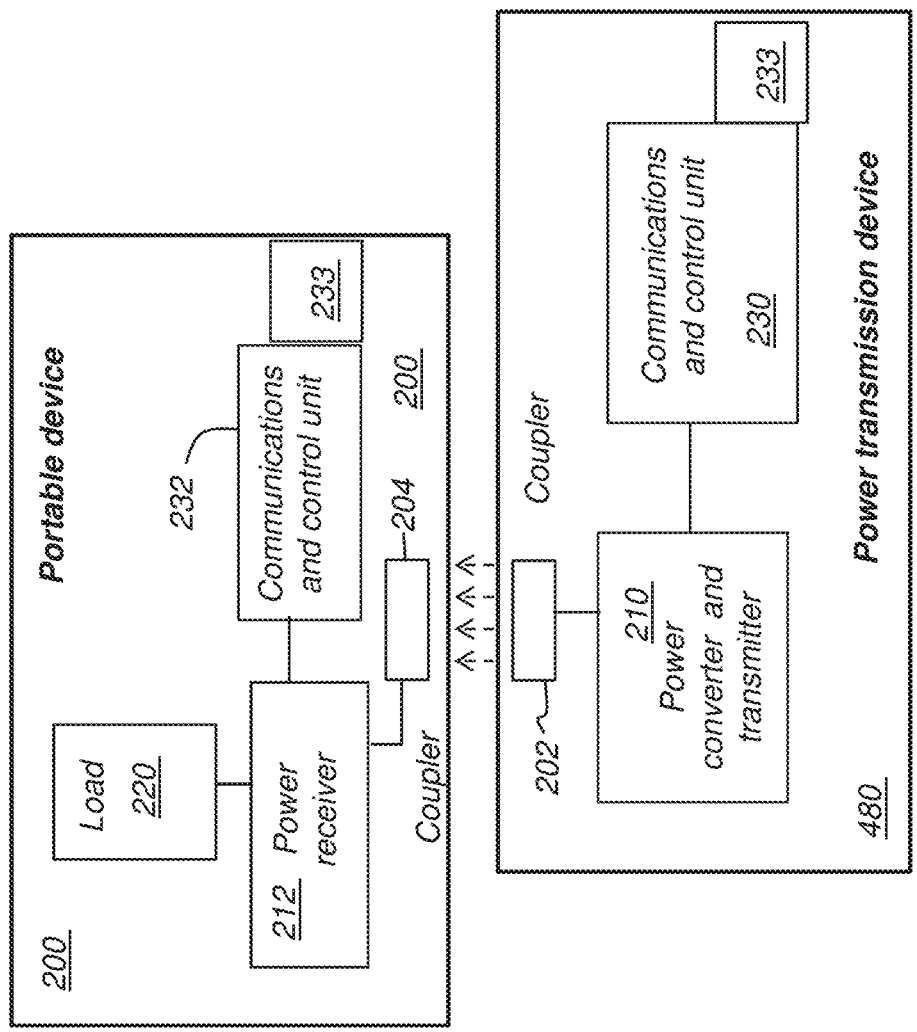
FIG. 4 is a schematic diagram that shows exemplary components cooperating to provide wireless power to a device.

The schematic diagram of FIG. 4 shows basic components for a wireless charging system, usable with the DR detector 10, that implements inductive charging or a similar wireless charging mechanism. Power transmission device 480, which can be provided on mobile radiographic system 400 as described herein, has a communications and control unit 230 and a power converter 210. Communications and control unit 230 coordinates and controls generation of the oscillating electromagnetic signals that are wirelessly transmitted to a portable device for providing power thereto. Power converter 210 provides an electromagnetic signal to a coupler 202, such as an inductive coupler, for transmission of high frequency signals to provide the power signal.

On portable device 200, such as DR detector 10 or other compatible devices, a corresponding wireless coupler 204 therewithin accepts the transmitted electromagnetic signal, which is converted to electrical energy for use by a load 220 such as for battery charging or directly used by a receiver 212. A communications and control unit 232 coordinates and controls power monitoring and delivery over the wireless coupler 204. The communications and control units 230 and 232 can be dedicated processors that handle power and recharging functions or can be processing logic components that control other functions for their respective devices. Communications and control units 230 and 232 can include a transponder 233 for enabling communication between power transmission and portable devices.

Frequencies used for charging can be appropriately specified to reduce the likelihood of interference to neighboring equipment. In general, the frequencies used are in the range of frequencies typically used for mobile phone communication (for example, 2.4 GHz), which are widely used among patients and staff in a hospital setting.

Figure 5:
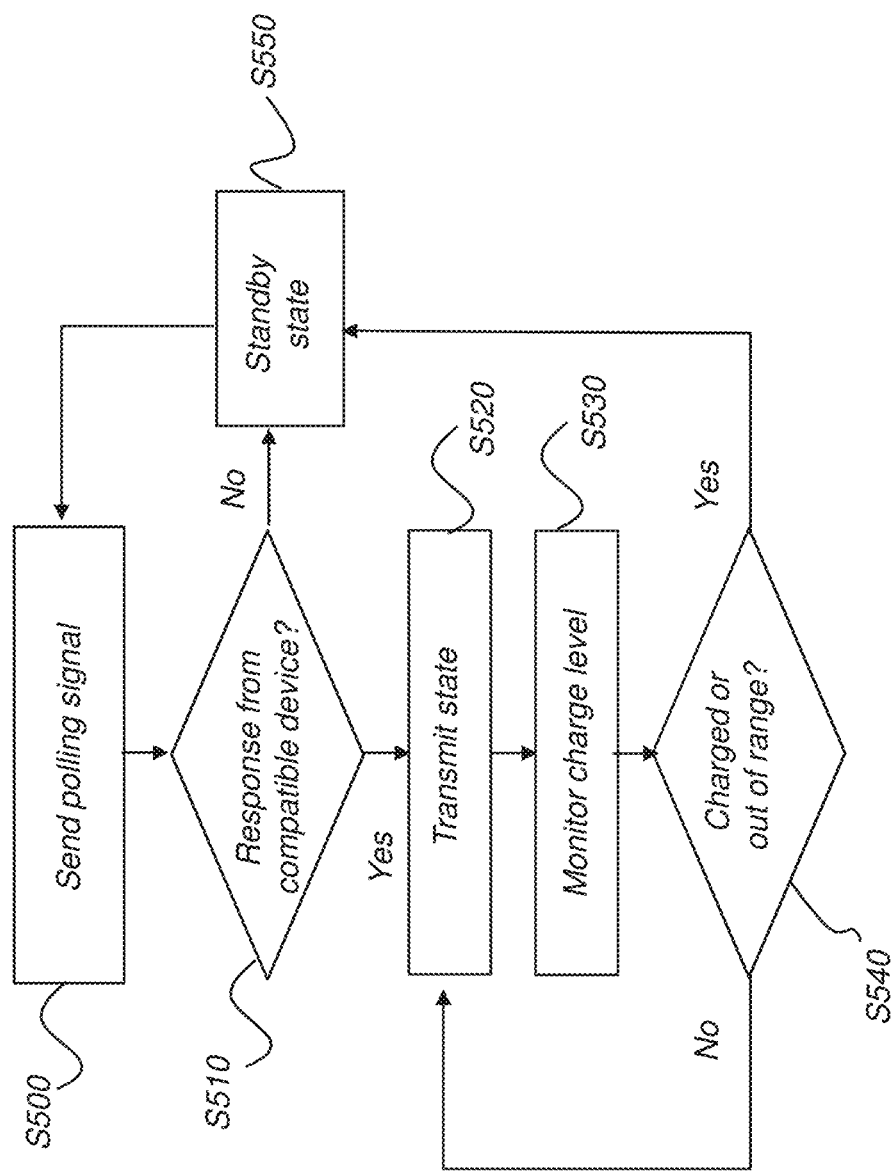
FIG. 5 is a logic flow diagram showing an exemplary method for wireless power transmission operation and control.

As described previously, the wireless power transmission device 480 of the present disclosure can be energized to transmit an RF power signal to an associated DR detector or other device that is programmed to receive a preselected frequency of the power signal. When outside the range of a compatible device needing charge, communications and control unit 230 can enter a standby state to reduce energy consumption. The logic flow diagram of FIG. 5 shows a method for power signal transmission according to one embodiment. In a polling step S500, communications and control unit 230 sends a low-energy wireless polling signal to determine whether or not there is a compatible DR detector 10 or other device within range that requires a charging power signal to be transmitted. A test step S510 checks for positive response. If there is no response, the system continues in a standby state S550, repeating the polling loop of steps S500, S510 and S550 periodically.

If a compatible device is detected, in test step S510, in the proximity of power transmission device 480 and responds positively, the system enters a transmit state S520, generating and transmitting the electromagnetic power signal that provides wireless power. The communications and control unit 230 monitors charge level in S530, and, at S540, if it determines the device is fully charged or the device is moved out of range, the system returns to standby state S550, else the power transmit state is maintained as S520.

In one embodiment, transmission of the electromagnetic power signal is directional, so that the signal comprises a vector between the power transmission device 480 and the target DR detector or other device that is being charged. Directional charging can be performed by energizing a portion of the transmitting antenna components or by actuating transmission components to direct the transmitted signal in the given direction. Multiple devices can be wirelessly charged at the same time. Devices can be configured for both wireless and wired charging.

According to an embodiment, the display 110 on transport frame 120 (FIG. 1) may be used to indicate charge status and to list one or more devices currently being charged and their relative charge level. This display can give the operator an indication of what devices require charging to provide needed performance.

Figure 6:
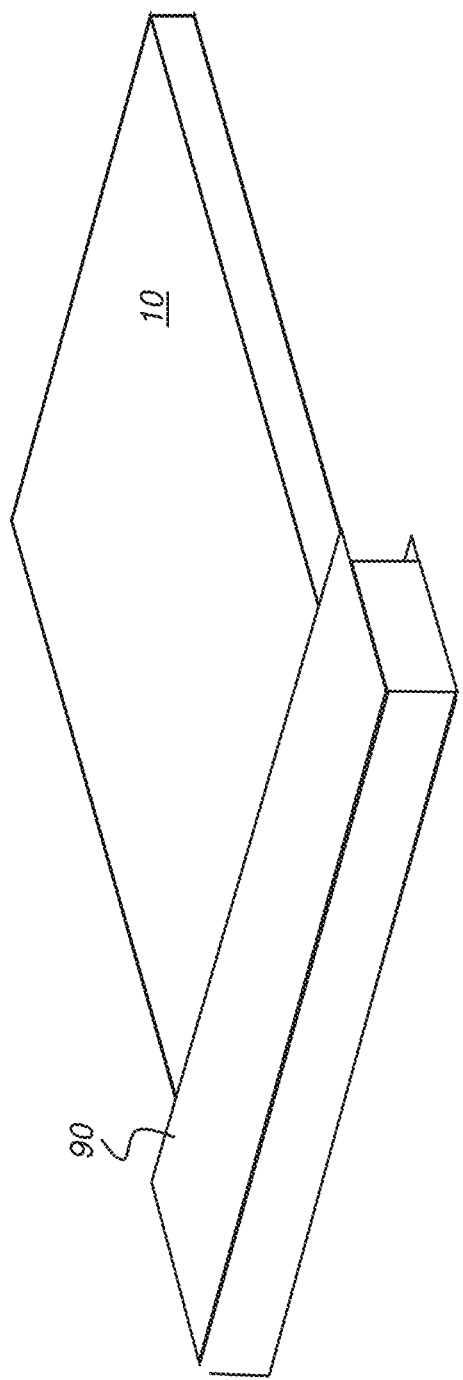
FIG. 6 is a perspective view that shows an exemplary charging sleeve seating a DR detector during wireless charging.

According to one embodiment, an attachment can be used in order to retrofit wireless recharging components in devices that were not manufactured to contain wireless recharging circuitry. FIG. 6 shows a charging sleeve 90 that is configured to receive and electrically connect to a DR detector 10 for wireless charging.

The RF charging signal can be directional, i.e., focused at the location of an identified device that needs to be charged. This arrangement allows efficient transmission of charging energy and reduced signal emission levels from the charging device. A detector or other device that needs to be recharged can request the recharging signal, enabling the power signal transmission circuitry to direct energy appropriately, without the need to broadcast the charging signal over a broad area.

Figure 7:
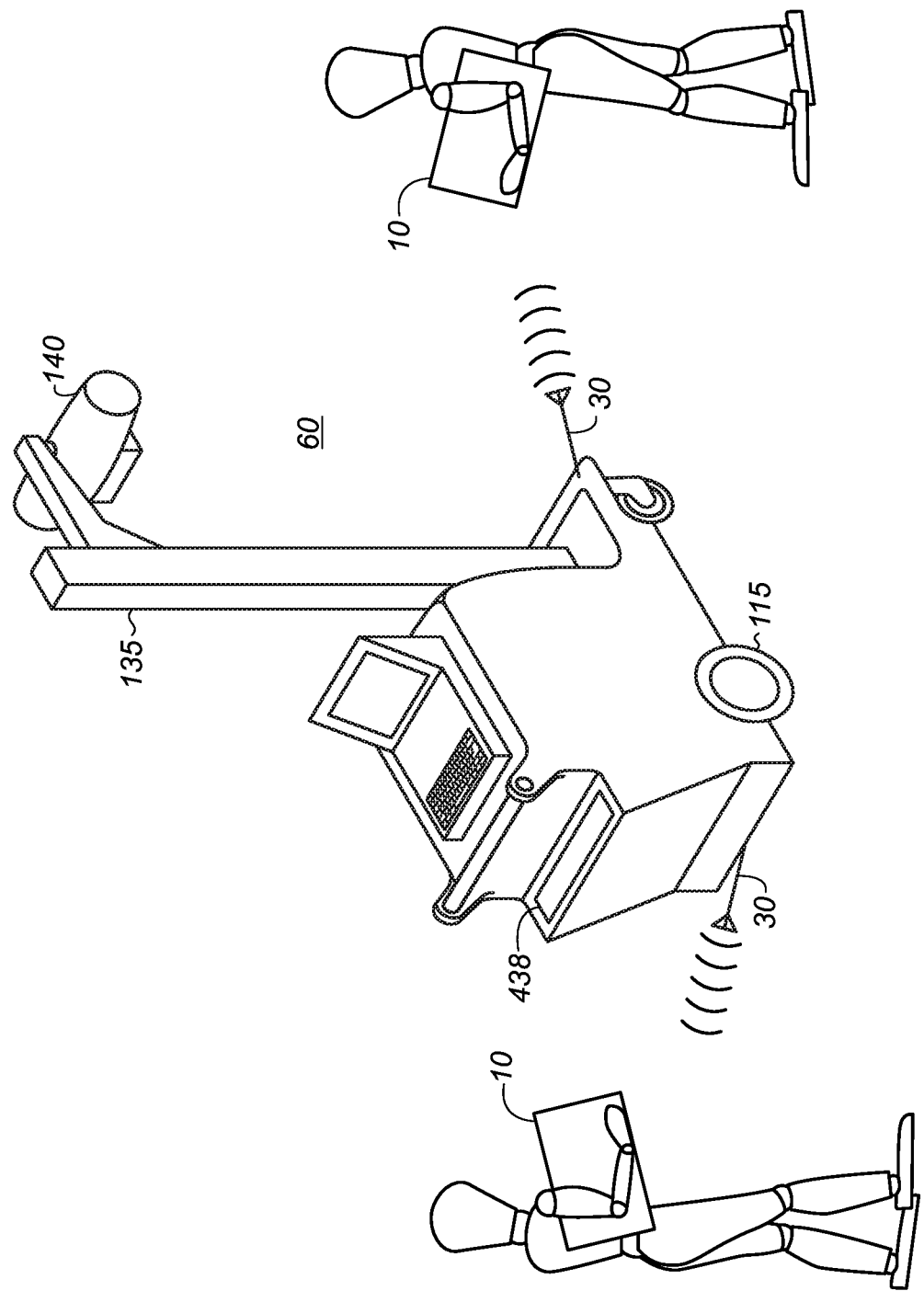
FIG. 7 is a schematic diagram that shows an exemplary configuration for focused wireless recharging directed to multiple devices.

FIG. 7 is a diagram of a mobile radiography apparatus 60 that is configured to adapt to the number, type, and location of rechargeable components. Wireless charging systems on the mobile radiography apparatus may be configured to detect and interact with rechargeable components that are within a radius that allows wireless recharging and that are configured for contactless recharging. Antennas 30 can provide the dual function of sensing and communication with the wirelessly rechargeable component, shown as DR detectors 10 in FIG. 7. In addition, antennas 30 can also direct a focused recharge signal to the rechargeable components, using energy direction and focus methods and apparatus known to those skilled in the wireless recharging arts. Focus configuration can be automated. In one embodiment, focus direction can be manually controlled.

As will be appreciated by one skilled in the art, aspects of the present invention may be embodied as a system, method, or computer program product. Accordingly, aspects of the present invention may take the form of a hardware and software embodiment (including firmware, resident software, micro-code, etc.), or an embodiment combining software and hardware aspects that may all generally be referred to herein as a "service," "circuit," "circuitry," "module," and/or "system."

GPS (Global Positioning Systems) or other external locator utility can alternately be used in order to detect and calculate proximity of a DR detector or other rechargeable device to the mobile radiography system. Once the proximity is detected, a polling signal can be transmitted in order to determine a transmission angle suitable for wirelessly transmitting a recharge signal. GPS information can be used directly to determine a direction for the recharging signal, with some level of accuracy. Positional measurement resolution can vary depending on the GPS protocol and support equipment used for signal reception and processing.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A mobile radiography system comprising:
a moveable transport frame configured to travel across a floor;
an adjustable support structure coupled to the moveable transport frame;
an x-ray source coupled to the adjustable support structure;
a power transmitter to transmit wireless power signals; and
a first battery powered digital detector to capture a radiographic image generated by x-rays from the x-ray source, the digital detector comprising receiving circuitry configured to receive the wireless power signals to recharge the battery,
wherein the first battery powered digital detector is configured to monitor a frequency of the transmitted wireless power signals, to not receive the transmitted wireless power signals, and to not recharge the battery only if the monitored frequency does not match a predetermined frequency range.

2. The system of claim 1, further comprising:
storage slots; and
a second battery powered digital detector,
wherein the first and second battery powered digital detectors each comprise a separate rechargeable battery and separate power signal receiving circuitry to receive the wireless power signals and to recharge the first and second battery powered digital detectors.

3. The system of claim 2, further comprising:
an electronic hand-held device comprising a display screen, a hand-held device rechargeable battery, and hand-held device power signal receiving circuitry to receive the wireless power signals and to recharge the hand-held device rechargeable battery.

4. The system of claim 2, wherein the separate rechargeable batteries are each configured to be removed from their corresponding digital detector and to receive the wireless power signals to recharge the separate rechargeable batteries rechargeable after being removed from their corresponding digital detector.

5. The system of claim 4, wherein the separate rechargeable batteries are each configured to be interchangeable as between the first and second battery powered digital detectors.

6. The system of claim 1, wherein the power transmitter comprises an array of micro-antennas.

7. The system of claim 2, wherein the first and second battery powered digital detectors are each configured to transmit a request for the power transmitter to start transmitting the wireless power signals.

8. The system of claim 7, wherein the first and second battery powered digital detectors are each configured to monitor a frequency of the transmitted wireless power signals and to receive the transmitted wireless power signals only if the monitored frequency matches a preselected frequency range.

9. The system of claim 7, wherein the first and second battery powered digital detectors each comprise a digital battery power monitoring circuit to measure a remaining power level of a battery therein, and wherein the first and second battery powered digital detectors are each further configured to automatically transmit the request for the power transmitter to start transmitting the wireless power signals in response to the digital battery power monitoring circuit indicating that the remaining power level of the battery therein is below a preset threshold.

10. The system of claim 1, further comprising a collimator, wherein the collimator comprises a collimator rechargeable battery and collimator power signal receiving circuitry to receive the wireless power signals and to recharge the collimator rechargeable battery.

11. The system of claim 2, wherein the power transmitter is configured to direct the wireless power signals toward the first battery powered digital detector and not toward the second battery powered digital detector.

12. The system of claim 2, wherein the power transmitter is configured to direct focused wireless power signals toward a separate selected one of the first and second battery powered digital detectors.

13. The system of claim 12, wherein the system is configured to display identifying information that identifies one or more of the first and second battery powered digital detectors that are being recharged by the transmitted wireless power signals.

14. The system of claim 1, further comprising an attachment assembly having a mobile power signal receiving circuit to receive the wireless power signals and to recharge a battery connected to the attachment assembly.

15. A mobile radiography system comprising:
a moveable transport frame configured to travel across a floor;
an adjustable support structure coupled to the moveable transport frame;
an x-ray source coupled to the adjustable support structure;
battery powered electronic devices associated with the mobile radiography system;
a power transmitter comprising one or more antennas to transmit wireless power signals; and
a digital transponder that is configured to transmit a polling signal to, and to receive a response signal from, any one or more of the battery powered electronic devices associated with the mobile radiography system,
wherein the response signal identifies a battery charge status for the corresponding any one or more of the battery powered electronic devices, the digital transponder is further configured to determine a relative location of the one or more battery powered electronic devices if its response signal indicates a battery charge level below a preset threshold, and wherein the digital transponder is further configured to align the one or more antennas to focus the transmitted wireless power signals toward the one or more of the battery powered electronic devices if its response signal indicates a battery charge level below the preset threshold.

16. The apparatus of claim 15, wherein the battery powered electronic devices comprise a digital radiography detector.

17. A method of recharging battery powered electronic devices, the method comprising:
wirelessly communicating with the battery powered electronic devices and determining their charge levels;
transmitting wireless power signals to one or more of the battery powered electronic devices whose charge levels are below a preselected threshold;
monitoring a charge level of the one or more battery powered electronic devices during the step of transmitting; and
terminating the step of transmitting in response to the charge level of the one or more battery powered electronic devices rising above a preset threshold.

18. The method of claim 17, further comprising automatically determining a spatial location of the one or more battery powered electronic devices using RF signals or GPS signals.

19. The method of claim 17, further comprising capturing a radiographic image in one of the battery powered electronic devices while transmitting the wireless power signals to said one of the battery powered electronic devices.

20. The method of claim 17, further comprising:
receiving one or more requests to transmit wireless power signals to one or more of the battery powered electronic devices; and
in response to receiving the one or more requests, transmitting wireless power signals to one or more of the battery powered electronic devices that transmitted the one or more requests.

* * * * *